(12) United States Patent
Knight

(10) Patent No.: US 7,435,749 B2
(45) Date of Patent: Oct. 14, 2008

(54) BEVERAGE TREATED WITH NICOTINE

(76) Inventor: Joseph R. Knight, 5737 Kanan Rd., #143, Agoura Hills, CA (US) 91301

( * ) Notice: Subject to any disclaimer, the term of this patent is extended or adjusted under 35 U.S.C. 154(b) by 0 days.

(21) Appl. No.: 10/497,375

(22) PCT Filed: Dec. 4, 2002

(86) PCT No.: PCT/US02/38655

§ 371 (c)(1),
(2), (4) Date: Jun. 3, 2004

(87) PCT Pub. No.: WO03/049552

PCT Pub. Date: Jun. 19, 2003

(65) Prior Publication Data

US 2004/0248946 A1    Dec. 9, 2004

Related U.S. Application Data

(60) Provisional application No. 60/372,385, filed on Apr. 15, 2002, provisional application No. 60/337,790, filed on Dec. 10, 2001.

(51) Int. Cl.
*A61K 31/44* (2006.01)
*A61K 36/81* (2006.01)

(52) U.S. Cl. ................... 514/343; 424/751
(58) Field of Classification Search ............. 514/343; 424/751
See application file for complete search history.

(56) References Cited

U.S. PATENT DOCUMENTS

| | | | | |
|---|---|---|---|---|
| 2,116,308 A | * | 5/1938 | Gore et al. | 426/432 |
| 2,128,043 A | * | 8/1938 | Garner | 546/279.4 |
| 2,162,738 A | * | 6/1939 | McCoy | 546/279.4 |
| 2,293,954 A | * | 8/1942 | Tiger et al. | 546/279.4 |
| 2,889,049 A | * | 6/1959 | Hauser | 210/476 |
| 3,901,248 A | | 8/1975 | Lichtneckert et al. | |
| 4,579,858 A | * | 4/1986 | Ferno et al. | 514/343 |
| 4,991,599 A | * | 2/1991 | Tibbetts | 131/297 |
| 5,135,753 A | | 8/1992 | Baker et al. | |
| 6,211,194 B1 | * | 4/2001 | Westman et al. | 514/300 |
| 6,268,386 B1 | * | 7/2001 | Thompson | 514/343 |
| 6,298,859 B1 | * | 10/2001 | Kierulff et al. | 131/297 |
| 6,344,222 B1 | | 2/2002 | Cherukuri et al. | |
| 6,358,060 B2 | | 3/2002 | Pinney et al. | |
| 6,472,222 B2 | | 10/2002 | Horst | |
| 6,479,076 B2 | | 11/2002 | Blank | |
| 2001/0014678 A1 | | 8/2001 | Cary | |
| 2002/0009533 A1 | * | 1/2002 | Fortune, Jr. | 426/594 |
| 2002/0054856 A1 | * | 5/2002 | Jones | 424/45 |
| 2002/0162563 A1 | * | 11/2002 | Williams | 131/352 |
| 2003/0103908 A1 | * | 6/2003 | Piskorz | 424/46 |

OTHER PUBLICATIONS

Remington's Pharmaceutical Sciences, 16th edition, published 1980, pp. 1382-1383.*
Remington's Pharmaceutical Sciences, 16th Edition, published 1980, pp. 1382-1384.*
Edward Leete, "Nicotine alkaloids", *McGraw-Hill Multimedia Encyclopedia of Science & Technology*, Copyright 1998, pp. 1-2, The McGraw-Hill Companies, Inc.
"Nicotine Polacrilex USP 10%", http://www.yogichem.com/nicotine10.htm, web page printed Nov. 13, 2002.
"Nicotine Polacrilex USP 18%", http://www.yogichem.com/nicotine18.htm, web page printed Nov. 13, 2002.
"FDA Grants Citizen's Petition Seeking Unapproved Drug Classification for 'Nicotine Water'", http://www.state.vt.us/atg/FDA%20Nicotine%20Water.htm, web page printed Nov. 13, 2002.
Mary M. Fanning, M.D., Ph.D., "Smoker's Attitudes Toward and Preferences in Nicotine Gums Findings From a Series of Personal Interviews", Medical Officer Review, Center for Drug Evaluation and Research; May 18, 1998, 3 sheets.
Glick, S.D. et al. Nature 1971 233:207-208 "Titration of oral nicotine intake with smoking behaviour in monkeys".

* cited by examiner

*Primary Examiner*—Raymond J Henley, III
(74) *Attorney, Agent, or Firm*—Joseph R. Knight

(57) ABSTRACT

The present application is directed to a method for preparing a solution containing processed nicotine and beverages made according to such method. The beverage produced according to this method does not have the discernible taste, smell or appearance of nicotine.

16 Claims, No Drawings

BEVERAGE TREATED WITH NICOTINE

CROSS-REFERENCE TO RELATED APPLICATIONS

This application is a National Phase Patent Application of International Application No. PCT/US02/38655, filed on Dec. 4, 2002, which claims priority of Provisional U.S. Patent Application No. 60/337,790, filed Dec. 10, 2001 and Provisional U.S. Patent Application No. 60/372,385, filed Apr. 15, 2002.

FIELD OF THE INVENTION

This invention relates to beverages for suppressing the desire to ingest nicotine.

BACKGROUND OF THE INVENTION

With the wide understanding of the health hazards caused by cigarette smoking, many efforts have been made to produce safer products which eliminate or reduce the need to smoke. For example, U.S. Pat. No. 3,901,248 to Lichtneckert, et al., discloses a chewable smoking substitute composition which includes nicotine adsorbed on a cation exchange resin, which is incorporated in a chewing gum base. When chewed, nicotine is released to diminish the urge to smoke.

More recently, U.S. Pat. No. 6,211,194 to Westman et al., and U.S. Pat. No. 6,268,386 to Thompson disclose beverages which have nicotine dissolved in them, and are intended to provide the consumer with sufficient nicotine to suppress the urge to smoke.

The problem with the prior art products is that the dissolved nicotine imparts a harsh or unpleasant taste.

SUMMARY OF THE INVENTION

This invention provides a beverage which has been treated with nicotine, but does not have any discernable nicotine taste or smell when consumed. In brief, the beverage is prepared by dissolving nicotine in water, and thereafter filtering the mixture to remove the taste and smell of nicotine from the water. In the preferred form, a nicotine containing substance is mixed with water, and the mixture is heated to a temperature above about 100° F., and preferably to the boiling point. The mixture is stirred while heating and preferably during boiling. Thereafter, the mixture is cooled, and filtered to eliminate the taste and smell of nicotine from the water.

The nicotine containing substance is selected from a group consisting of tobacco alkaloids, which include nicotine and nicotine-like or related pharmacologically active compounds such as nor-nicotine, lobeline and the like, as well as the free-base substance nicotine and all pharmacologically acceptable salts of nicotine, including acid addition salts. Nicotine salts are useful and include nicotine hydrogen tartrate and nicotine bitartrate, as well as nicotine hydrochloride, nicotine dihydrochloride, nicotine sulfate, nicotine citrate, nicotine zinc chloride monohydrate and nicotine salicylate, either alone or in combination. "Nicotine" is used herein to include all the foregoing tobacco alkaloids and nicotine salts. "Nicotine" also includes the solid complex of one or more tobacco alkaloid compounds bound to an ion exchange resin, or other polymer release system, particularly a cation exchanger. Examples of nicotine ion exchange resins are set forth in U.S. Pat. No. 3,901,248 to Lichtneckert et al., referred to above. That patent is incorporated herein in full. Nicotine polacrilex is especially preferred as a source of nicotine. Other sources include cured tobacco leaves and other plants which contains sufficient nicotine to be effective.

When nicotine polacrilex (a powder) is mixed with water, the material does not readily go into solution at room temperature, but instead produces a slurry. Heating and stirring the slurry causes the nicotine polacrilex to go into solution or at least become thoroughly dispersed. When the solution is cooled, much of the ion exchange resin solidifies and forms a precipitate which settles out of the mixture, which is preferably cooled to about room temperature, and thereafter filtered through activated charcoal to remove so much of the nicotine that it can no longer be detected by taste or smell. Preferably, the cooled solution is passed through a mechanical filter before passing through the charcoal filter. The processed water can also be filtered through an ionic filter, such as a semi-permeable membrane used in reverse osmosis processes.

DETAILED DESCRIPTION OF THE INVENTION

Nicotine in any suitable form, such as tobacco leaves, nicotine alkaloids, or the various other sources of nicotine mentioned above, is mixed with water, and heated, preferably to the boiling point, and stirred vigorously for about one to about thirty minutes. The mixture is allowed to cool, permitting any solids present to settle out. The supernatant liquid is then filtered to reduce the amount of nicotine in the liquid to a level so low that it cannot be detected by taste, odor, or color.

In one presently preferred form of the invention, the nicotine is in the form of nicotine polacrilex in which nicotine is bound to an ion-exchange resin, as described in U.S. Pat. No. 3,901,248 referred to above. Nicotine polacrilex in powder form is commercially available from Spectrum Chemical Mfg. Corp. in Gardena, California 90248. Twenty-five grams of nicotine polacrilex (15%, U.S.P.) was mixed in three gallons of water to form a slurry, which was heated to the boiling point (about 210° F.) while stirring for five to ten minutes. The nicotine polacrilex powder appeared to dissolve, or at least liquefy, so that it was uniformly dispersed in the mixture. Thereafter, the mixture was allowed to stand and cool to about room temperature. During the cooling process, a precipitate formed and settled to the bottom of the mixture. Supernatant liquid, which had a brownish color was taken from the mixture and passed through a 0.2 μm polyethersulfone (PES) membrane filter, and then through a medical grade granular activated carbon filter, producing a water-white filtrate, which was tasteless, odorless and colorless. Analysis of the filtrate for nicotine with high pressure liquid chromatography did not show any measurable amount of nicotine.

The PES membrane filter is available from PTI Advanced Filtration Inc. in Oxnard, California 93030. The activated carbon filter is available from ResinTech Inc., in Cherry Hill, N.J. 08034 1409.

The filtered product can be consumed as drinking water, and has proved useful in suppressing the urge to smoke cigarettes. For example, many smokers have suppressed the urge to smoke by drinking about 500 ml of the treated water when experiencing the urge to smoke.

The product of this invention can also be mixed with vitamins, fruit flavoring, cola mix, and natural fruit juices to provide a variety of beverages with the benefit described above.

The product of this invention may also be used in alleviating the symptoms of attention deficit hyperactive disorder (ADHD), attention deficit disorder (ADD), Toureete's Syndrome, Schizophrenia, Parkinson's Disease, Alzheimer's Disease, anxiety, and depression.

What is claimed is:

1. A method for preparing a solution containing processed nicotine, the method comprising:
   a) stirring a mixture comprising nicotine and water at a temperature above about 100° F. for at least 5 minutes; and thereafter
   b) filtering the mixture;
   wherein said solution comprises processed nicotine and water with no other alkaloid.

2. A method for preparing a solution containing processed nicotine the method comprising:
   a) stirring a mixture comprising water and nicotine for at least five minutes at a temperature above about 150° F.;
   b) cooling the mixture to room temperature; and
   c) filtering the mixture.

3. The method according to claims 1 or 2 in which said mixture comprising nicotine and water is made with nicotine polacrilex.

4. The method according to claims 1 or 2 in which said mixture is stirred at about 212° F. for at least about five minutes.

5. The method according to claims 1 or 2 in which said mixture is stirred and boiled for at least about five minutes.

6. The method according to claims 1 or 2 in which said filtering step comprises filtering the mixture through activated carbon.

7. The method according to claims 1 or 2 in which said filtering step comprises filtering the mixture through a permeable membrane.

8. A beverage which contains a solution containing processed nicotine wherein said processed nicotine is prepared by:
   a) stirring a mixture comprising nicotine and water at a temperature above about 100° F. for at least five minutes; and thereafter
   b) filtering the mixture;
   wherein said beverage comprises processed nicotine and water with no other alkaloid.

9. The beverage of claim 8 wherein said stirring step is at a temperature above 150° F. for at least five minutes.

10. A beverage which contains a solution containing processed nicotine wherein said processed nicotine is prepared by:
    a) stirring a mixture comprising nicotine and water at a temperature above about 100° F. for at least five minutes;
    b) cooling the mixture to room temperature; and
    c) filtering the mixture.

11. The method according to claims 1 or 2 in which said filtering step comprises filtering the mixture through a semipermeable membrane.

12. The method according to claims 1 or 2 in which said filtering step comprises filtering the mixture through a mechanical filter.

13. A method for preparing a solution containing processed nicotine, the method comprising:
    a) stirring a mixture comprising nicotine and water at a temperature above about 100° F. for at least 5 minutes; and thereafter
    b) filtering the mixture;
    wherein said solution consists of processed nicotine, water, and at least one additive wherein said at least one additive is chosen from the group consisting of vitamins, fruit flavoring, cola mix and natural fruit juices.

14. The method of claim 13 wherein said solution comprises processed nicotine, water, and at least one fruit flavoring with no other alkaloid.

15. A beverage which contains a solution processed nicotine wherein said processed nicotine is prepared by:
    a) stirring a mixture comprising nicotine and water at a temperature above about 100° F. for at least five minutes; and thereafter
    b) filtering the mixture;
    wherein said beverage consists of processed nicotine, water, and at least one additive wherein said at least one additive is chosen from the group consisting of vitamins, fruit flavoring, cola mix, and natural fruit juices.

16. The beverage of claim 8 wherein said beverage comprises processed nicotine, water, and at least one fruit flavoring, with no other alkaloid.

* * * * *